United States Patent
Anderson et al.

(10) Patent No.: US 12,070,236 B2
(45) Date of Patent: Aug. 27, 2024

(54) VALVULOPLASTY MEDICAL DEVICE THAT ALLOWS BLOOD FLOW DURING USE

(71) Applicant: C.R. BARD, INC., Tempe, AZ (US)

(72) Inventors: Tyson Anderson, Chandler, AZ (US); Corey Rousu, Cave Creek, AZ (US)

(73) Assignee: C.R. BARD, INC., Franklin Lakes, NJ (US)

( * ) Notice: Subject to any disclaimer, the term of this patent is extended or adjusted under 35 U.S.C. 154(b) by 0 days.

(21) Appl. No.: 17/629,952

(22) PCT Filed: Aug. 23, 2019

(86) PCT No.: PCT/US2019/047817
§ 371 (c)(1),
(2) Date: Jan. 25, 2022

(87) PCT Pub. No.: WO2021/040675
PCT Pub. Date: Mar. 4, 2021

(65) Prior Publication Data
US 2022/0249108 A1    Aug. 11, 2022

(51) Int. Cl.
*A61B 17/22*    (2006.01)
*A61B 17/00*    (2006.01)

(52) U.S. Cl.
CPC .... *A61B 17/22* (2013.01); *A61B 2017/00783* (2013.01); *A61B 2017/22055* (2013.01)

(58) Field of Classification Search
CPC ........... A61B 2017/22048; A61B 2017/22051; A61B 2017/22055; A61B 2017/22065; A61B 2017/22067; A61B 2017/22068; A61B 2017/22069; A61B 2017/22071
See application file for complete search history.

(56) References Cited

U.S. PATENT DOCUMENTS

| | | | |
|---|---|---|---|
| 5,545,135 A | 8/1996 | Iacob et al. | |
| 7,384,411 B1* | 6/2008 | Condado | A61N 5/1007 604/103.05 |
| 2009/0030503 A1* | 1/2009 | Ho | A61B 17/1204 623/1.24 |
| 2011/0144742 A1* | 6/2011 | Madrid | A61F 2/2433 623/2.11 |
| 2012/0116439 A1* | 5/2012 | Ho | A61F 2/2427 606/194 |
| 2013/0190796 A1* | 7/2013 | Tilson | B29C 53/60 606/192 |
| 2018/0036032 A1 | 2/2018 | Spencer et al. | |
| 2018/0318560 A1* | 11/2018 | Sanchez Garcia | A61M 25/1002 |
| 2019/0083259 A1 | 3/2019 | Le et al. | |

FOREIGN PATENT DOCUMENTS

WO    2011084500 A2    7/2011

\* cited by examiner

*Primary Examiner* — Martin T Ton
(74) *Attorney, Agent, or Firm* — Dickinson Wright PLLC; Andrew D. Dorisio

(57) ABSTRACT

Medical devices are described including a plurality of expandable members to open a vascular lumen while maintaining blood flow during expansion. The device includes a plurality of exterior members (114) that are inflatable or expandable. The device may also include, but does not require, an inner member (110) to further radially expand or circumferentially separate the exterior members.

15 Claims, 4 Drawing Sheets

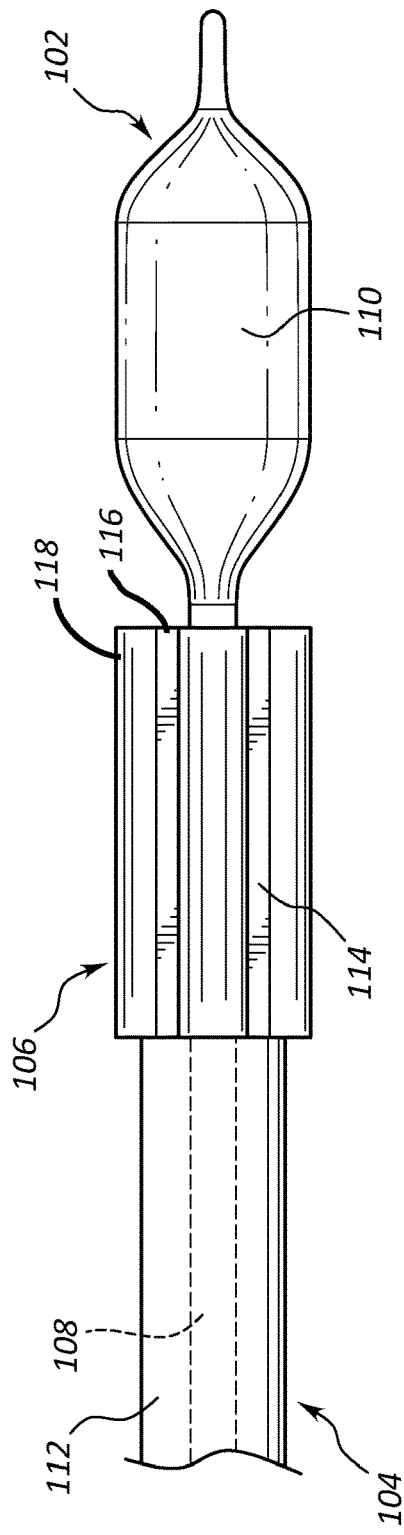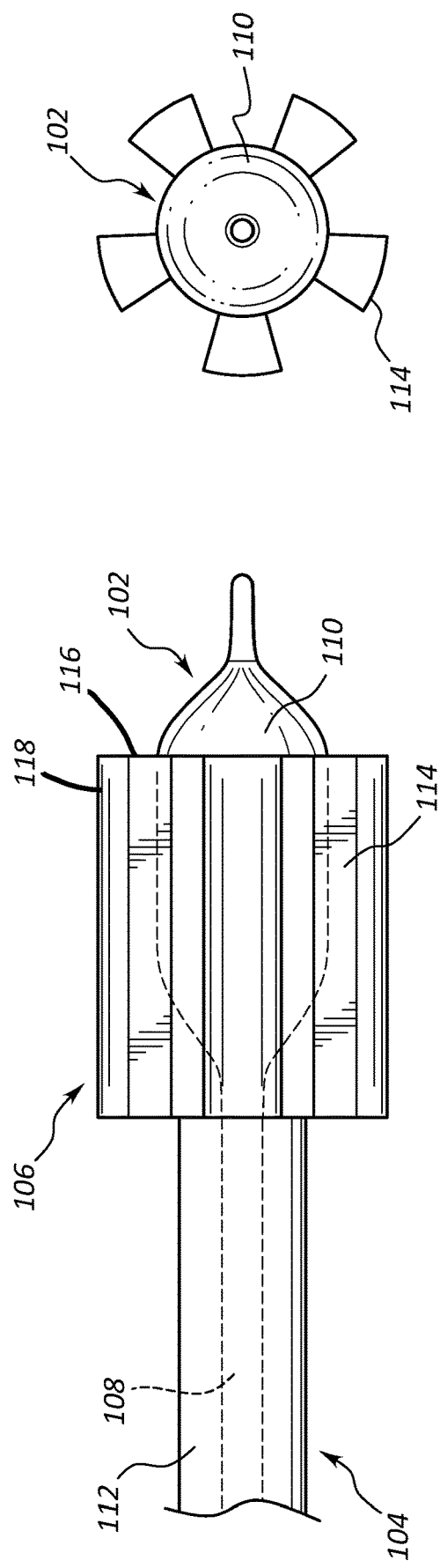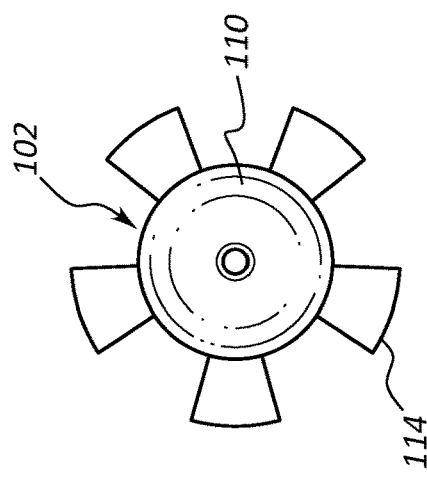

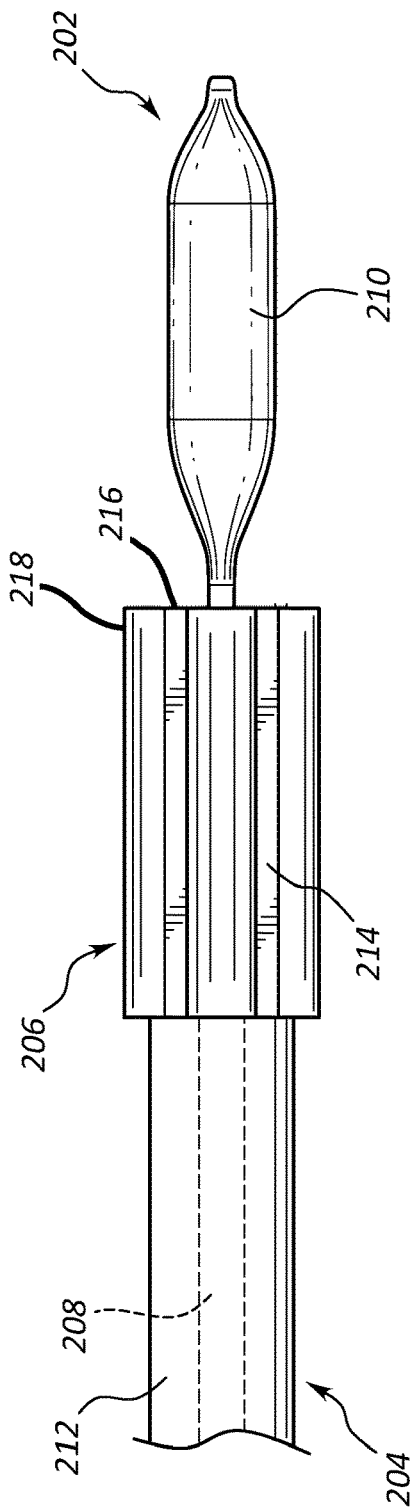
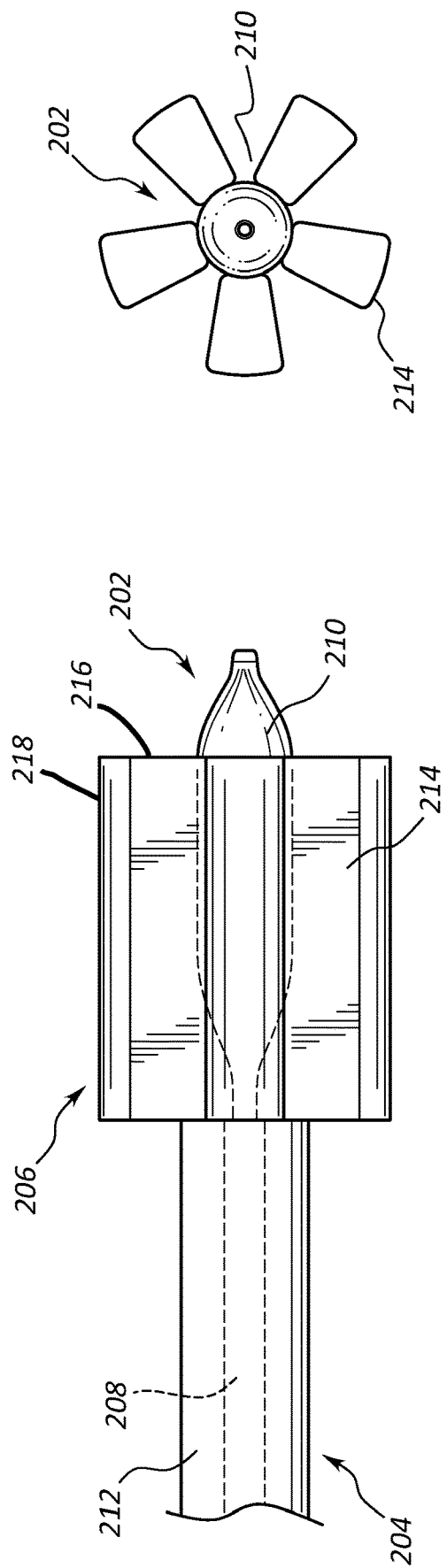
FIG. 2A
FIG. 2B
FIG. 2C

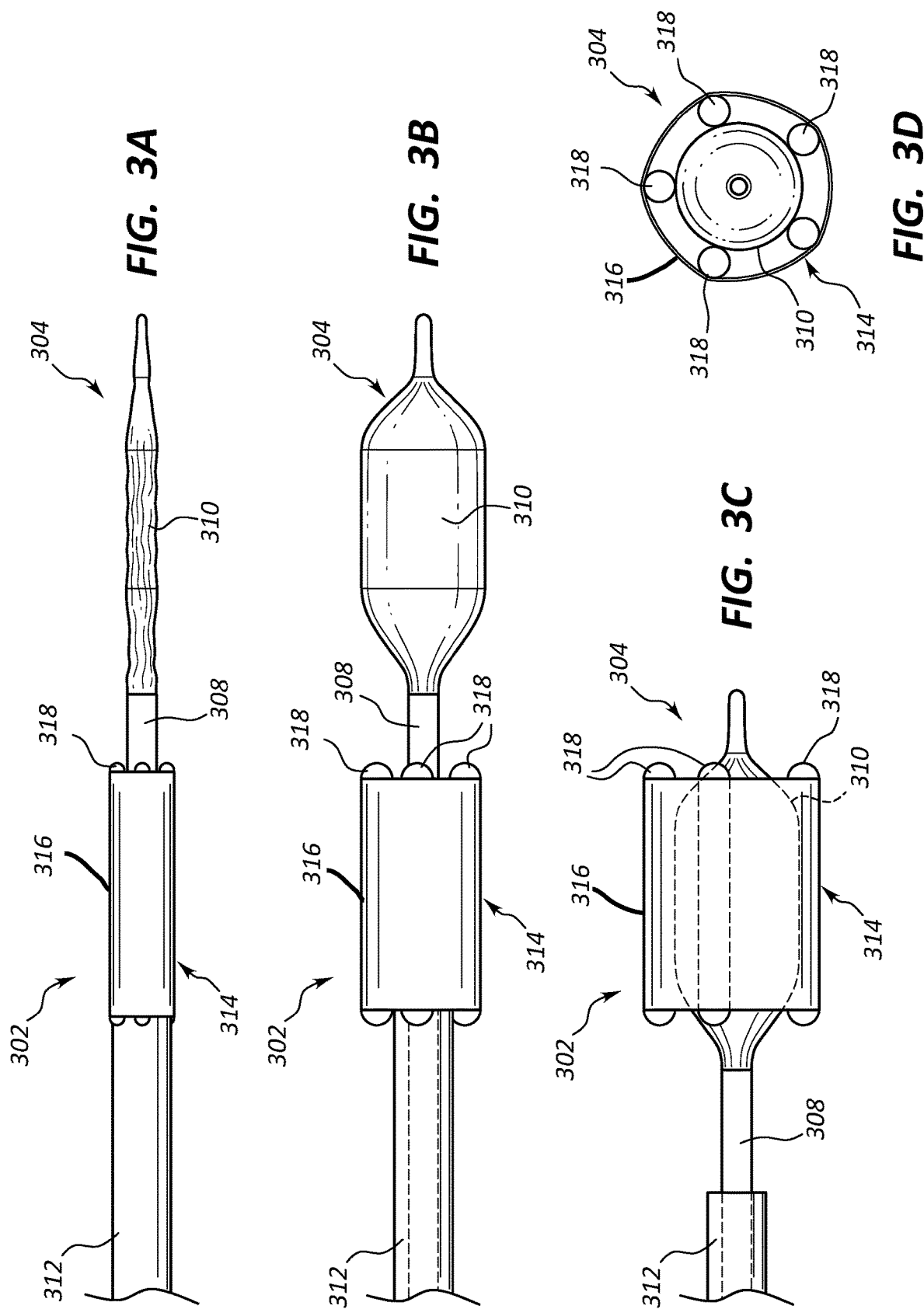

VALVULOPLASTY MEDICAL DEVICE THAT ALLOWS BLOOD FLOW DURING USE

BACKGROUND

Conventional valvuloplasty devices include an expandable section to open stenotic valves. In order to open the valve and provide a proper force profile across its surface, these devices typically must block blood flow during use. For example, a balloon may be inflated at a distal end of a catheter. When the balloon is inflated, the cross section of the vasculature lumen is blocked by the balloon, which prevents blood flow during the procedure.

SUMMARY

Exemplary embodiments described herein include a medical device with an expandable section, in particular with passages or spaces to permit fluid flow during use. The device may include a distal tip with an expanding (expandable) member surrounded by one or more exterior members. The expanding member or exterior members may expand, inflate, or open. When expanded, inflated, or opened, an exterior surface of the exterior members move radially outward and a gap may be available between the exterior members to pass fluid longitudinally past the device.

In an exemplary embodiment, the device is a medical device used for valvuloplasty. The valvuloplasty device includes a catheter and a distal tip and has a reduced configuration and an expanded configuration. In the expanded configuration, the distal tip may be expanded to open up stenotic valves, while still allowing blood flow to occur. The distal tip may include one or more features of the exemplary configurations described herein in any combination. The valvuloplasty device may include an inner member and an outer member having a plurality of exterior members. The inner member, the outer member, any one or more of the exterior members, and any combination thereof may be expanded such that an exterior surface of the exterior members move radially outward from a longitudinal axis of the device. When expanded, the exterior members may include gaps, spaces, tunnels, or other passages that allows blood to flow during use.

DRAWINGS

FIGS. 1A-1C illustrate an exemplary valvuloplasty device according to embodiments of the invention.

FIGS. 2A-2C illustrate an exemplary valvuloplasty device according to embodiments of the invention.

FIGS. 3A-3D illustrate an exemplary valvuloplasty device according to embodiments of the invention.

DESCRIPTION

Figure 4:
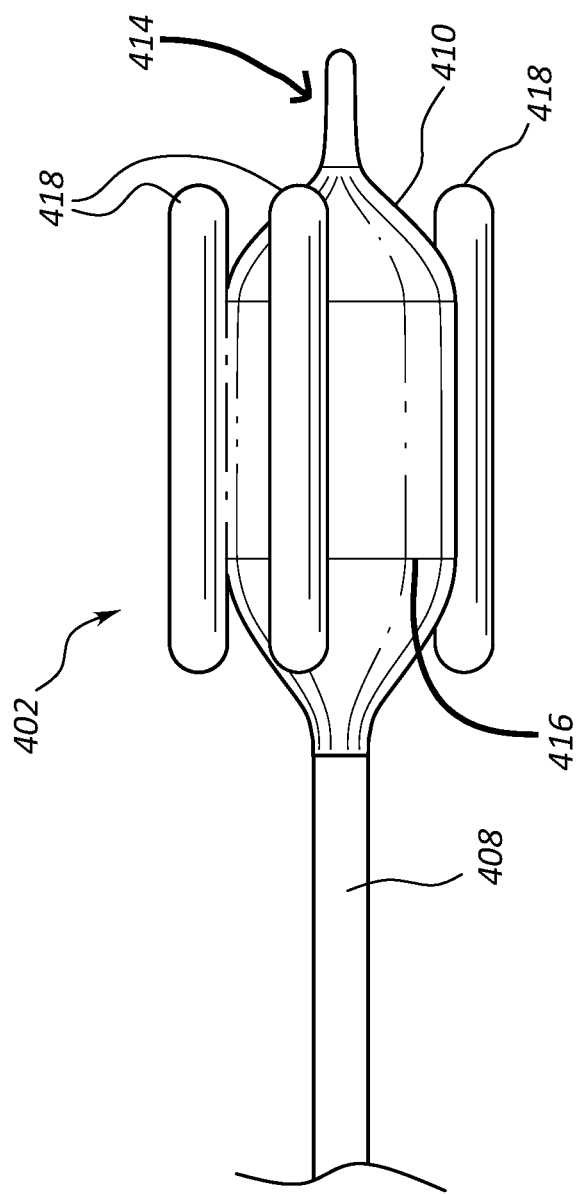
FIG. 4 illustrates an exemplary valvuloplasty device according to embodiments of the invention.

The following detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention. It should be understood that the drawings are diagrammatic and schematic representations of exemplary embodiments of the invention, and are not limiting of the present invention nor are they necessarily drawn to scale.

Valvuloplasty devices are described, optionally including a plurality of expandable members to open a stenotic valve while maintaining blood flow during expansion. The device may include a plurality of exterior members that are inflatable or expendable. The device may also include, but does not require, an inner member to further radially expand or circumferentially separate the exterior members.

Although embodiments of the invention may be described and illustrated herein in terms of use with valvuloplasty, it should be understood that embodiments of this invention are not so limited, but are additionally applicable to other medical procedures, optionally in which an outer surface of a device needs to be expanded, while maintaining a fluid flow path along the device.

FIGS. 1A-1C illustrate an exemplary valvuloplasty device 102 having an inner member 104 and outer member 106. The inner member 104 may be configured to be movable within and relative to the outer member 106, and radially expand the outer member 106. The outer member 106 includes a plurality of individual members 114 that expand and separate.

The outer member 106 may include a proximal end 112 and distal end 114. The proximal end 112 may be any device to retain and control the distal end from outside of the body. Therefore, the proximal end 112 is configured to push the distal end through the vasculature to the stenotic valve and remove the distal end from the body once the procedure is complete. In an exemplary embodiment, the proximal end 112 may be a tube, such as a catheter. Other proximal ends may also be used, such as wires, guide wires, tubes, rods, etc. The distal end 114 may be configured to collapse to reduce an outer radial profile of the device for navigation through the vasculature and expand within the patient's vasculature, while maintaining fluid flow longitudinally past the device.

In an exemplary embodiment, the distal end 114 of the outer member 106 may include a plurality of individual members 118 and a connecting device 116. The connecting device 116 may be an extension of the proximal end 112, separate from the proximal end 112, or may be one or more integrated or separate connectors between individual members 118. For example, the connecting device 116 may be a catheter, tube, ring, or bands that couple adjacent individual members 118. The connecting device 116 may be expandable or collapsible. For example, the connecting device 116 may be elastic or flexible. In an exemplary embodiment, the connecting device 116 is a ring or tube, and the individual members 118 are attached to an exterior surface of the connecting device 116. The connecting device 116 may be flexible such that it may be folded in a collapsed configuration bringing the individual members 118 toward each other, in close proximity, or in contact. The connecting device 116 may be expandable by unfolding the connecting device 116 thus increasing an outer radial profile of the individual members and connecting device. The connecting device 116 may also be elastic or otherwise expandable, such as inflatable. The individual members 118 or the connecting device 116 may include a biased configuration, such that the outer member 106 is in a collapsed configuration when not expanded by the inner member 104.

The inner member 104 may include a proximal end 108 and distal end 110. The proximal end 108, similar to the exterior member proximal end 112 may be configured to navigate or control the distal end from outside of the body. The proximal end 108 may be configured to push the distal end 110 through the vasculature to the stenotic valve and remove the distal end from the body once the procedure is complete. In an exemplary embodiment, the proximal end 110 may be a tube, such as a catheter. Other proximal ends may also be used, such as wires, guide wires, tubes, rods, etc. The distal end 110 may be configured to expand the distal end 114 of the exterior member 106.

In an exemplary embodiment, the distal end 110 of the inner member 104 may be collapsible/expandable or may have a static profile. The distal end 110 may be moved relative to the distal end 114 of the outer member 106. The distal end 110 of the inner member 104 may be positionable radially within the distal end 114 of the exterior member. Once within the distal end of the exterior member, the distal end of the interior member may be configured to expand the distal end of the exterior member. For example, a profile of the interior member 104 distal end 110 may be tapered such that translating the interior member distal end to a position toward or within the distal end of the outer member expands the outer member. The interior member 104 may also be inflatable such that once positioned within the distal end 114 of the exterior member, it may be enlarged to expand the individual members 118.

As shown and described, the individual members 118 and distal end 110 of the inner member 104 may be solid or hollow and of constant or dynamic cross sectional profile. For example, these may be flexible, solid rod or cylindrical shaped components. These may also be flexible, hollow rods or cylindrical shaped components. These may also be inflatable components. These members may have various cross sectional dimensions and shapes. The distal or proximal ends may be tapered to define a desired longitudinal profile. The cross-sectional profile may be circular, ovoid, wedge-shaped, or other geometric shape.

Exemplary features are now provided with respect to specific exemplary embodiments. Any of the features described herein may be used in any combination with any of the embodiments or features described herein.

FIGS. 2A-2C illustrate an exemplary embodiment with an expandable outer member 206 and constant profile inner member 208.

As shown, the outer member 206 includes a proximal end 212 and distal end 214. The proximal end 212 is a tube, such as a catheter. The catheter may include one or more lumens. For example, the catheter may include a lumen in which the proximal end 208 of inner member may be positioned. The catheter may also include one or more other lumens as needed by the procedure. For example, a guidewire lumen may be used either within the outer member or within the inner member, inflation lumens, flushing lumens, drug delivery lumens, and other conventional catheter features may also be included in either the inner or outer members.

The outer member 206 distal end 214 may include a plurality of individual members 218 connected by connecting device 216. The connecting device 216 includes one or more bands between individual members 218 that attach adjacent members together. Connecting device 216 may be flexible such that it has a collapsed configuration by folding the connecting device and an expanded configuration by unfolding the connecting device between individual members. The connecting device 216 may, alternatively or in addition thereto, be elastic, such that upon application of a force the length of the connecting device 216 or the distance between individual members 218 may be changed or increased. The individual members may have a cross sectional profile to create a circumferentially continuous outer perimeter when the device is in a collapsed configuration.

The cross sectional profile of an individual member may be pie-shaped. An exterior surface of the individual members may be curved circumferentially and have a longer circumferential length than an inner surface of the individual member. The lateral facing sides of the individual members may be shaped to increase the available fluid flow past the device in the expanded configuration. The lateral sides may also be contoured to accommodate the connecting device 216 in the collapsed configuration. For example, the arc length in degrees at a radial distal along the individual member between the lateral sides or at the inner surface of the individual member may be less than the arc length in degrees at the exterior surface of the individual member. The distal end surface of the individual members 218 may also be contoured to approximate or mate with the proximal region of the inner member 204 distal end 210. For example, the inner surface of a distal region of the distal end 214 of the outer member 206 may have an outward taper toward the distal direction to correspond to the taper of the proximal region of the inner member 204 distal end 210.

As shown, the inner member 204 includes a proximal end 208 and distal end 110. The proximal end 208 is a rod or wire. For example, various configurations similar to conventional guide wires may be used. The distal end 210 includes a static profile enlarged section. The distal end 210 may be solid or hollow. The distal end 210 may be flexible such that it may bend or curve along the longitudinal direction. The distal end 210 may also be rigid in that it is sufficiently strong to maintain a constant outer profile and not collapse when expanding the distal end of the outer member.

The proximal end 208 of inner member 204 may have an outer diameter less than an inner diameter of the proximal end 212 inner diameter of the outer member 206. A proximal region of the distal end 210 of the inner member 204 may be outwardly tapered from the proximal end 208 of the inner member 204 toward a distal region of the distal end. The distal end 210 may have a constant diameter section distal the proximal region with an outer diameter greater than an inner diameter of the distal end 214 of the outer member 206 in a collapsed configuration or in a relaxed configuration. The length of the constant diameter section of the inner member 204 distal end 210 may be approximately as long, as long, or longer than the length of the individual members 218. A distal region of the distal end 210 of the inner member 204 may be inwardly tapered in a distal direction from the constant diameter section to a smaller end diameter. The tip of the inner member 204 may also be configured to assist the device in navigation. Therefore, the distal tip may be of a smaller diameter and flexible to navigate tortious vascular passages.

The device may have a collapsed, delivery profile in which the inner member is positioned within the outer member with the distal end 210 of the inner member extending distally past and abutting the distal end 214 of the outer member 206. In the collapsed configuration, the individual members 218 may be in contact with adjacent members, and the connecting device 216 folded or contained within spaces circumferentially between individual members 218. The device may then be navigated through the vasculature and positioned at a desired deployment site. The device may then be expanded by longitudinally moving the distal end 210 of the inner member 204 proximally relative to the distal end 214 of the outer member 206. As the outer surface of the distal end 210 translates relative to the inner surface of the distal end 214, the increasing diameter of the distal end 210 pushes the individual members 218 of the outer member radially outward and apart. As the individual members 218 expand, the connecting device 216 unfolds or stretches. After the procedure, the inner member 210 may be translated distally to remove the distal end 210 from inside the outer member 206 and permit the individual members 218 of the outer member 206 to collapse.

In an exemplary embodiment, the connecting device or other actuator may be used to collapse the individual members after deployment. For example, one or more connecting devices, or separate tether may be coupled between the inner member 204 and outer member 206. When the distal end 210 of the inner member 204 is translated out of the distal end 214 of the outer member 206, the actuator may pull the individual members closed.

FIGS. 3A-3D illustrate an exemplary embodiment with an expandable outer member 303 with expandable individual members 318 and inner member 308 having an expandable distal end 310.

As shown, the outer member 303 may have a proximal end 312 and distal end 314. The proximal end may be a catheter having one or more lumens extending to the distal end. In the illustrated embodiment, the catheter has at least two lumens, one for passage of the proximal end of the inner member 304 and at least one for an inflation fluid to the individual members 318. The distal end 314 includes a plurality of individual members 318. The individual members may be inflatable. The individual members 318 may be in fluid communication such that injection of inflation fluid through the inflation lumen fills the individual member, individual members, or a subset of individual members. Any combination of individual members may be coupled and filled separately through the same or different inflation methods or through the same or different inflation lumens.

In an exemplary embodiment, the plurality of individual members is filled simultaneously with the injection of a single inflation fluid. For example, a single inflation lumen may be used to fill the plurality of individual members. The connecting device 316 may incorporate a fluid communication path between adjacent individual members. The single inflation lumen may also individually couple to a distal region or end of each of the individual members and fill the individual members in parallel. Filling the individual members simultaneously or in parallel does not require that the inflation of each member occur exactly at the same time. The reference to simultaneous is intended to merely distinguish the filling of the individual members sequentially in which each previous individual member would be filled or substantially filled before the next individual member begins to fill. Therefore, simultaneous filling includes any overlap in the filling of all of the individual members, such that at least some of each of the individual members is still being filled when each of the other members are also being filled.

The individual members may have an inflated configuration to increase the outer surface area of an exterior perimeter of the inflated individual members, while simultaneously increasing the open, flow-through area between individual members towards an interior of the device. Therefore, an inflated cross section of the individual members may be wedge or pie shaped such that an exterior surface end is larger than an interior surface end. The individual members may also have any other geometric, inflated cross section, such as circular, ovoid, or pear shaped.

As shown, the inner member 304 includes a proximal end 308 and distal end 310. The proximal end 308 may be a catheter with one or more lumens. In the example shown, proximal end 308 has at least one inflation lumen to the distal end 310 of the member, which comprises an expandable balloon. The balloon may have a longitudinal profile with a constant diameter section. The constant diameter section may be approximately as long as, as long as, or longer than the distal end 314 of the outer member 303 to evenly expand the outer member at the deployment site. The distal end 310 balloon may also include one or both tapered ends in the inflated configuration, similar to the configuration of FIG. 2A.

In an exemplary embodiment, an outer sleeve 320 may circumscribe the plurality of individual members to create a uniform exterior surface. The outer sleeve 320 may be used as the connecting device 316 or in addition thereto. Similar to the connecting device, the outer sleeve may be elastically expandable, may be folded or flexibly expandable, may be inflatable, or may otherwise accommodate the expansion of the individual members. The outer sleeve may be connected to the individual members or otherwise to either the inner or outer members. The outer sleeve may also be used as the biasing component to reduce the profile of the outer member distal end after the inner member has been retracted or removed from the outer member.

The valvuloplasty device 302 may comprise a collapsed/deflated configuration and an expanded/inflated configuration. The device may have an initial configuration with the inner member 304 positioned within the outer member 306 with the distal end 310 of the inner member either extending past the distal end of the outer member or positioned within the outer member. Positioning the inner member distal end, including the expandable member, distal the end of the outer member may reduce the overall delivery profile of the device, as the inflatable members of the inner member 310 and the outer member 318 are longitudinally staggered. Once at the desired location, the individual members 318 and/or inner member 304 distal end 310 can be inflated, sequentially or simultaneously. The inner member 304 may be translated proximally into the distal end 314 of the outer member 306 to further expand the individual members 318. The inner member 304 may be positioned within the outer member 306 before or after inflation of either the individual members 318 or inner member distal end 310.

FIG. 4 illustrates an exemplary embodiment of a valvuloplasty device 402 with the inner and outer members integrated into a single unit. As shown, a proximal end 408 of the device comprises a catheter. The catheter may include one or more lumens, such as inflation lumen(s), guidewire lumens, etc. The distal end 414 of the device 402 includes a plurality of inflatable members 410, 418. A first or central inflatable member 410 is at a distal end of the catheter 408 and may align with a central axis of the catheter. The central inflatable member 410 has a longitudinal length and may have characteristics similar to those described above with respect to inner member distal end. Around an exterior surface of the central inflatable member 410 is a plurality of exterior inflatable members 418. The plurality of exterior inflatable members 418 may be coupled to the central inflatable member 410 or to the proximal end 408 or other portions of the device 402. The central inflatable member 410 and the plurality of exterior inflatable members 418 are arranged parallel, aligned longitudinally, and positioned at spaced intervals circumferentially around the exterior surface of the central member 410 and connected by a connecting device 416. The plurality of individual members 418 and central member 410 may be in fluid communication and share a common inflation lumen or may be separately inflated. For example, the plurality of exterior inflatable members 418 may be in fluid communication and inflate simultaneously, while the central inflatable member 410 may inflate separately.

In an exemplary embodiment, the valvuloplasty device 402 has a collapsed configuration and an expanded configuration. In the collapsed configuration, the central member 410 and the exterior members 418 are deflated and folded/wrapped to form a reduced diameter delivery configuration. Once positioned at the desired location within the patient, the central member 410 and the exterior members 418 are inflated together or sequentially.

The valvuloplasty device 402 may also include a force limiting assembly to limit or control a desired amount of inflation force imposed by the inflatable/expandable members. In an exemplary embodiment, the device may include a pressure regulator to control the inflation pressure of one or more of the expandable members. The device may also be controlled by a spring or other force regulator to apply a desired pressure to the patient.

The valvuloplasty devices described herein may also include an actuation or control device at a proximal end to control the position, actuation, or relative location of the members during operation.

Exemplary embodiments may integrate the inner member and outer member in different ways. For example, the inner member distal end and outer member distal end may remain separated and movable relative to each other, while sharing a common proximal end. The device may also include various combinations of the features described, including different combinations of the inflatable, expandable, or rigid distal ends (110, 210, 310, 410) and individual members (118, 218, 318, 418). The device may also include any combination or attributes of the connecting device 116, 216, 216, 416. Therefore, any feature may be added, removed, subdivided, duplicated, or otherwise rearranged or recombined and remain within the scope of the present description.

This disclosure may be considered to relate to the following items:

1. A medical device for valvuloplasty, comprising:
    an inner member comprising an inner member proximal region and an inner member distal region, the inner member distal region including an expandable member; and
an outer member comprising an outer member proximal region and an outer member distal region, the outer member distal region including a plurality of individual members circumferentially separated from each other. The medical device may be configured to open a stenotic valve while maintaining blood flow during expansion of the expandable member.
2. The device of item 1, wherein the outer member proximal region comprises a tube and the outer member distal region comprises a connector between the plurality of individual members, wherein the plurality of individual members are connected such that a gap is provided between adjacent individual members of the plurality of individual members, and/or wherein the inner member distal region is longitudinally moveable relative to the outer member distal region.
The gap may be configured to pass fluid longitudinally past the device.
3. The device of item 1 or item 2, the device comprising a deployed configuration and a collapsed configuration with a reduced profile, wherein, optionally, if dependent on item 2, the gap between adjacent individual members of the plurality of individual members is present in the deployed configuration.
4. The device of any of items 1-3, wherein the gap extends for a longitudinal length and/or an entire radial distance of adjacent individual members.
5. The device of any of items 1-4, wherein the plurality of individual members are inflatable.
6. The device of any of items 1-5, wherein the plurality of individual members maintain a constant cross sectional profile in the collapsed configuration and the deployed configuration.
7. The device of any of items 1-6, wherein the expandable member is inflatable.
8. The device of any of items 1-7, wherein the expandable member maintains a constant cross sectional profile in the collapsed configuration and the deployed configuration.
9. The device of any of items 1-8, wherein, in the deployed configuration, the expandable member defines a tapered proximal region, a constant diameter intermediate region, and a tapered distal region.
10. The device of any of items 1-9, wherein, in the deployed configuration, the plurality of individual members comprise constant profile sections coextensive along at least a portion of the constant diameter intermediate region.
11. The device of any of items 1-10, the device comprising a deployed configuration and a collapsed configuration with a reduced profile, wherein
    the inner member proximal region comprising a tube and the inner member distal region comprising an inflatable member, the inflatable member have an inflated profile defining a tapered proximal region a constant profile intermediate region and a tapered distal region, the inner member comprising a distal end extending from the tapered distal region;
    the outer member proximal region comprising a tube positioned circumferentially around a portion of the inner member proximal region, the outer member distal region comprises a connector between the plurality of individual members and the plurality of individual members are inflatable,
    in the deployed configuration the plurality of individual members comprise constant profile sections coextensive along at least a portion of the constant profile intermediate region and the plurality of individual members are connected such that a gap is provided between adjacent individual members of the plurality of individual members.
The medical device may be configured to open a stenotic valve while maintaining blood flow during expansion of the expandable member and/or the gap may be configured to pass fluid longitudinally past the device.
12. A medical device for valvuloplasty, comprising:
    a proximal region defining a tube; and
    an expandable distal region comprising an interior expandable member and a plurality of exterior individual members radially outside of the interior expandable member and circumferentially spaced around interior expandable member, the plurality of exterior individual members being inflatable.
13. The medical device of item 12, further comprising an inflated configuration and a collapsed configuration with a reduced profile, wherein the plurality of exterior individual members are circumferentially positioned such that in the inflated configuration a gap is maintained between adjacent individual members of the plurality of exterior individual members and the interior expandable member is inflatable.
14. The medical device of item 12 or item 13, wherein the proximal region, expandable distal region including the interior expandable member and plurality of exterior individual members are integrally formed.

15. The medical device of any of items 12-14, further comprising an expandable medical device positioned within a portion of the proximal region of the medical device and extending distal the expandable distal region, the expandable medical device comprising a mandrel end configured to move proximally relative to the expandable distal region and expand the interior expandable member and move the plurality of exterior individual members radially outward and circumferentially separate adjacent exterior individual members.

The medical device of any of items 12 to 15 may have the features of any of items 1 to 11 or 16 to 20.

16. A medical device, comprising:
    a proximal end comprising a tube; and
    a distal end comprising an expandable section and two or more exterior members radially exterior the expandable section,
    wherein the medical device has a collapsed configuration and a deployed configuration, the deployed configuration having an increased outer profile diameter as compared to the collapsed configuration and having the two or more exterior members circumferentially separated and out of contact along a longitudinal length.

17. The medical device of item 16, further comprising an inner mandrel device and an exterior expandable device, the exterior expandable device comprising the tube and exterior members, and wherein the inner mandrel device is separate from the exterior expandable device.

18. The medical device of item 15 or item 16, wherein the tube, expandable section, and two or more exterior members are integrally formed.

19. The medical device of any of items 15-18, wherein the two or more exterior members are inflatable.

20. The medical device of any of items 15-19, wherein in the deployed configuration the expandable section comprises a tapered distal region, a tapered proximal region, and a generally constant diameter intermediate region.

The medical device of any of items 16 to 20 may have the features of any of items 1 to 15.

Although embodiments of this invention have been fully described with reference to the accompanying drawings, it is to be noted that various changes and modifications will become apparent to those skilled in the art. Such changes and modifications are to be understood as being included within the scope of embodiments of this invention as defined by the appended claims.

The invention claimed is:

1. A medical device for valvuloplasty, comprising:
   an inner member comprising an inner member proximal region and an inner member distal region, the inner member distal region including an expanding member; and
   an outer member comprising an outer member proximal region and an outer member distal region, the outer member distal region including a plurality of individual members circumferentially separated from each other;
   wherein the outer member proximal region comprises a tube and the outer member distal region comprises an expandable connector attached to the plurality of individual members, the connector forming a ring shape, wherein the connector is separate from the tube,
   wherein the plurality of individual members are connected such that a gap is provided between adjacent individual members of the plurality of individual members, and the inner member distal region is longitudinally moveable relative to the outer member distal region.

2. The device of claim 1, the device comprising a deployed configuration and a collapsed configuration with a reduced profile, wherein the gap between adjacent individual members of the plurality of individual members is present in the deployed configuration.

3. The device of claim 2, wherein the gap extends for a longitudinal length and an entire radial distance of adjacent individual members.

4. The device of claim 2, wherein the plurality of individual members are inflatable.

5. The device of claim 2, wherein the plurality of individual members each maintain a constant cross sectional profile in the collapsed configuration and the deployed configuration.

6. The device of claim 2, wherein the expanding member is inflatable.

7. The device of claim 2, wherein the expanding member maintains a constant cross sectional profile in the collapsed configuration and the deployed configuration.

8. The device of claim 2, wherein, in the deployed configuration, the expanding member defines a tapered proximal region, a constant diameter intermediate region, and a tapered distal region.

9. The device of claim 8, wherein, in the deployed configuration, the plurality of individual members each comprise constant profile sections coextensive along at least a portion of the constant diameter intermediate region.

10. The device of claim 1, the device comprising a deployed configuration and a collapsed configuration with a reduced profile, wherein
    the inner member proximal region comprising a tube and the inner member distal region comprising an inflatable member, the inflatable member having an inflated profile defining a tapered proximal region, a constant profile intermediate region and a tapered distal region, the inner member comprising a distal end extending from the tapered distal region;
    the outer member proximal region comprising a tube positioned circumferentially around a portion of the inner member proximal region, the outer member distal region comprises a connector between the plurality of individual members and the plurality of individual members are inflatable,
    in the deployed configuration, the plurality of individual members comprise constant profile sections coextensive along at least a portion of the constant profile intermediate region and the plurality of individual members are connected such that a gap is provided between adjacent individual members of the plurality of individual members.

11. The device of claim 1, wherein the connector is elastic.

12. The device of claim 1, wherein the connector is flexible.

13. The device of claim 1, wherein the connector is a tube.

14. A medical device for valvuloplasty, comprising:
    a proximal region defining a tube; and
    an expandable distal region comprising an interior expanding member forming a ring shape and a plurality of exterior individual members radially outside of the interior expanding member and circumferentially spaced around and attached to the interior expanding member, the plurality of exterior individual members being inflatable;

further comprising an expanding medical device positioned within a portion of the proximal region of the medical device and extending distal the expandable distal region, the expanding medical device comprising a mandrel end configured to move proximally relative to the expandable distal region and expand the interior expanding member and move the plurality of exterior individual members radially outward and circumferentially separate adjacent exterior individual members, wherein the mandrel end is inflatable to be collapsible and expandable.

15. A medical device, comprising:

a proximal end comprising a tube; and a distal end comprising an expandable section and two or more exterior members radially exterior the expandable section, wherein the medical device has a collapsed configuration and a deployed configuration, the deployed configuration having an increased outer profile diameter as compared to the collapsed configuration and having the two or more exterior members circumferentially separated and out of contact along a longitudinal length;

further comprising an inner mandrel device and an exterior expandable device, the exterior expandable device comprising the tube and an expandable connector attached to the exterior members, the expandable connector forming a ring shape, and wherein the inner mandrel device is separate from the exterior expandable device, wherein the inner mandrel device is configured to move proximally relative to the exterior expandable device and expand the exterior members and move the exterior members radially outward and circumferentially separate adjacent exterior members.

* * * * *